United States Patent [19]
Mita et al.

[11] Patent Number: 5,278,269
[45] Date of Patent: Jan. 11, 1994

[54] FILM-FORMING RESIN AND HAIR DRESSING COMPOSITION CONTAINING THE SAME

[75] Inventors: Katsumi Mita, Chiba; Takashi Oda, Wakayama; Hiromi Yamamoto, Chiba; Akihiro Kondo, Wakayama, all of Japan

[73] Assignee: Kao Corporation, Tokyo, Japan

[21] Appl. No.: 448,049

[22] Filed: Dec. 8, 1989

[30] Foreign Application Priority Data

Dec. 9, 1988 [JP] Japan ................. 63-309821

[51] Int. Cl.⁵ ........................... C08F 220/56
[52] U.S. Cl. ................. 526/303.1; 424/47; 424/70; 424/DIG. 1; 424/DIG. 2; 526/307
[58] Field of Search .............. 526/307, 303.1; 424/DIG. 1; DIG. 2; 47, 70

[56] References Cited

U.S. PATENT DOCUMENTS

| | | | |
|---|---|---|---|
| 4,237,253 | 12/1980 | Jacquet et al. | 526/75 |
| 4,324,780 | 4/1982 | Jacquet et al. | 424/47 |
| 4,440,744 | 4/1984 | Strasilla et al. | 526/307 |
| 4,842,852 | 6/1989 | Nowak, Jr. et al. | 424/71 |

Primary Examiner—Paul R. Michl
Assistant Examiner—John J. Guarriello
Attorney, Agent, or Firm—Sughrue, Mion, Zinn, Macpeak & Seas

[57] ABSTRACT

A film-forming resin which is a copolymer comprising specific monomers and a hair dressing composition containing the film-forming resin are disclosed. This film-forming resin is highly compatible in LPG and thus useful in the replacement of conventionally employed Freon gas by LPG. The hair dressing composition shows excellent effects including a good set-retention.

5 Claims, 1 Drawing Sheet

FILM-FORMING RESIN AND HAIR DRESSING COMPOSITION CONTAINING THE SAME

FIELD OF THE INVENTION

This invention relates to a film-forming resin and a hair dressing composition containing the same.

BACKGROUND OF THE INVENTION

Film-forming resins have been added to hair dressing composition such as hair spray and set lotion in order to impart various effects including setting and set-retention to these products. Examples of commonly employed film-forming resins include polyvinyl pyrrolidone, polyvinyl pyrrolidone/vinyl acetate copolymer and vinyl acetate/crotonic acid copolymer.

A film-forming resin conventionally contained in a hair dressing composition would show a certain degree of set-retention under commonly employed conditions. Under highly humid condition, however, the adhesiveness and fluidity thereof would be increased by moisture absorption, which makes it impossible to effectively retain a hair set. On the other hand, a hair dressing composition should be readily washed away with the use of a shampoo. That is to say, a film-forming resin to be added to a hair dressing composition should have a high solubility in water as well as a low hygroscopicity. It is difficult to simultaneously satisfy these conflicting requirements. Thus it is frequently observed to give up to achieve a high solubility of a film-forming resin in water and employ other solvent or a mixture of solvents.

Freon gas, which has been widely used as a propellants hitherto in various aerosol compositions, is an ideal propellants from the viewpoints of chemical stability, combustibility and toxicity. Recently, however it has been pointed out that Freon gas might cause an environmental problem, namely, the breakage of the ozone layer. Therefore a tendency to replace Freon gas with incompletely halogenated ones or propellants free from any halogen atom is seen lately. Examples of such propellants include hydrocarbons (LPG) such as propane, butane, isobutane and mixtures thereof. However a film-forming resin generally shows a lower solubility in LPG than in Freon gas. When the propellant in a conventional aerosol composition is simply replaced with LPG, therefore, the film-forming resin in the aerosol composition would be precipitated and thus the product cannot be used any longer. Accordingly it is required to use a larger amount of a solvent such as ethanol or isopropyl alcohol in a spray in order to fully dissolve the film-forming resin in the LPG. When sprayed, the hair dressing composition product thus obtained forms a thick and heavy mist, which makes it difficult to give a beautiful hair set.

Furthermore, some setting products such as hair spray make the hair coarse or rough after drying.

Further there are some additional problems such that the resin film thus formed on the surface of the hair peels off when brushed, namely, so-called flaking, and that the gloss of the hair is deteriorated.

SUMMARY OF THE INVENTION

Under these circumstances, we have conducted extensive studies. As a result, we have found out that the above-mentioned problem can be solved by using a specific copolymer as a film-forming resin, thus completing the present invention.

Accordingly, the present invention provides a film-forming resin which is a copolymer comprising the following monomers (a) to (d):

(a) 30 to 80% by weight of a (meth)acrylamide monomer represented by the following formula (I):

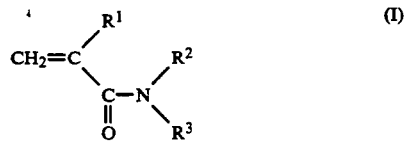

wherein $R^1$ represents a hydrogen atom or a methyl group; and $R^2$ and $R^3$ may be either the same or different from each other and each represents a hydrogen atom or an alkyl group having 4 to 12 carbon atoms, or $R^2$ and $R^3$ form a ring together with the adjacent nitrogen atom;

which will be called the monomer (I) hereinafter;

(b) 5 to 45% by weight of a (meth)acrylate monomer represented by the following formula (II):

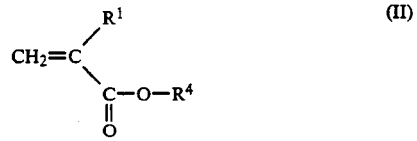

wherein $R^1$ is as defined above; and
$R^4$ represents an alkyl group having 1 to 4 carbon atoms;

which will be called the monomer (II) hereinafter;

(c) 2 to 30% by weight of a (meth)acrylate monomer and/or a (meth)acrylamide monomer having a tertiary amino group, represented by the following formula (III):

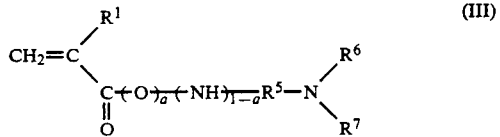

wherein $R^1$ is as defined above;
$R^5$ represents an alkylene group having 2 or 3 carbon atoms;
$R^6$ and $R^7$ may be either the same or different from each other and each represents a methyl or an ethyl group; and
$a$ is an integer of 0 or 1;
which will be called the monomer (III) hereinafter; and (d) 0 to 30% by weight of a (meth)acrylate monomer represented by the following formula (IV):

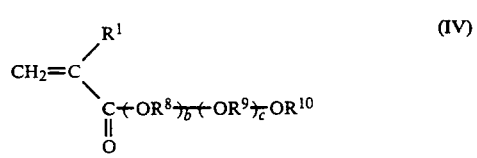

wherein $R^1$ is as defined above;

R[8] and R[9] are different from each other and each represents an alkylene group having 2 to 4 carbon atoms;

R[10] represents a hydrogen atom or a methyl group; and b and c are each an integer of 0 to 50, provided that b and c are not 0 at the same time;

which will be called the monomer (IV) hereinafter; and a hair dressing composition containing the above film-forming rein.

DETAILED DESCRIPTION OF THE INVENTION

Figure 1:
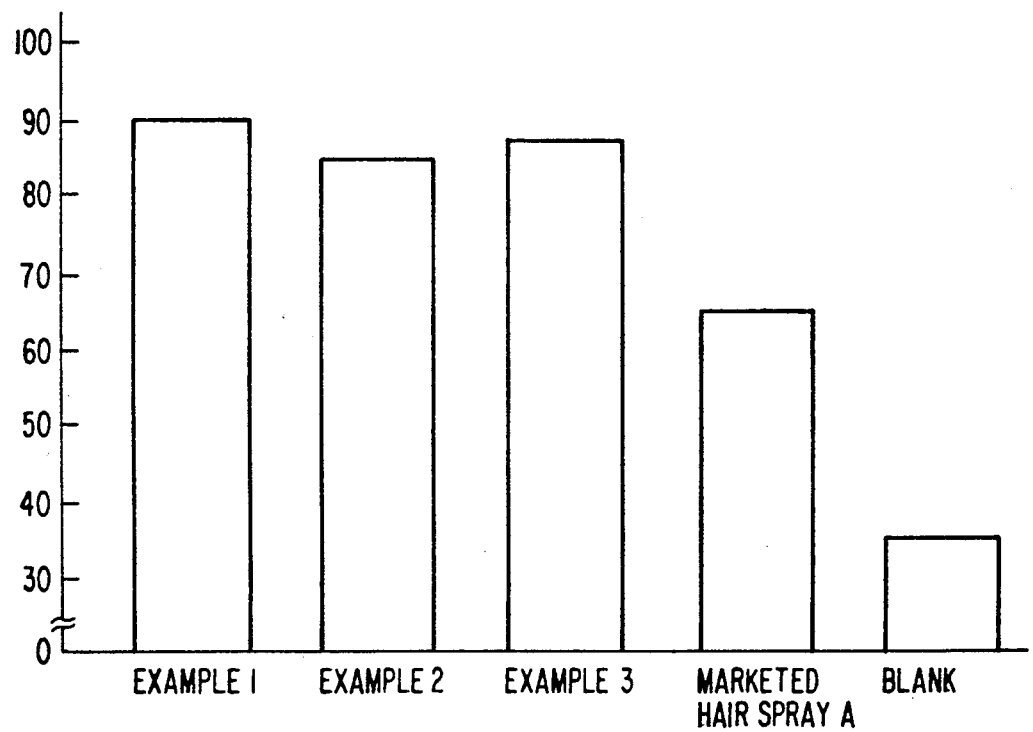
FIG. 1 shows curl-retention ratios of the products of the present invention and a marketed hair spray under highly humid conditions.

Examples of the monomer (I) to be used in the production of the film-forming resin of the present invention include (meth)acrylamide (the term "(meth)acryl-" as used herein means "acryl- or methacryl-"), N-n-butyl(meth)acrylamide, N-t-butyl(meth)acrylamide, N-octyl(meth)acrylamide, N-lauryl(meth)acrylamide and (meth)acryloylmorpholine. Among these materials, N-butyl(meth)acrylamide, N-octyl(meth)acrylamide and N-lauryl(meth)acrylamide are particularly preferable. Either one of these materials or a mixture thereof can be used in an amount of 30 to 80% by weight, preferably 40 to 70% by weight, of the total monomers.

Examples of the monomer (II) include methyl (meth)acrylate, ethyl (meth)acrylate, propyl (meth)acrylate and butyl (meth)acrylate. Among these materials, methyl (meth)acrylate, ethyl (meth)acrylate and butyl (meth)acrylate are preferable, and ethyl (meth)acrylate is more preferable. Either one of these materials or a mixture thereof can be used in an amount of 5 to 45% by weight, preferably 10 to 40% by weight, of the total monomers.

Examples of the monomer (III) include N,N-dimethylaminoethyl (meth)acrylate, N,N-diethylaminoethyl (meth)acrylate, N,N-dimethylaminopropyl (meth)acrylate and N,N-dimethylaminopropyl(meth)acrylamide. Among these materials, N,N-dimethylaminoethyl (meth)acrylate, N,N-diethylaminoethyl (meth)acrylate and N,N-dimethylaminopropyl(meth)acrylamide are preferable, and N,N-dimethylaminoethyl (meth)acrylate is more preferable. Either one of these materials or a mixture thereof can be used in an amount of 2 to 30% by weight, preferably 5 to 15% by weight, of the total monomers.

Examples of the monomer (IV) include hydroxyethyl (meth)acrylate, hydroxypropyl (meth)acrylate, polyethylene glycol mono(meth)acrylate, polypropylene glycol mono(meth)acrylate, methoxypolyethylene glycol mono(meth)acrylate and methoxypolypropylene glycol (meth)acrylate. Among these materials, polyethylene glycol mono(meth)acrylate and methoxypolypropylene glycol mono(meth)acrylate are preferable, and methoxypropylene glycol mono(meth)acrylate is more preferable. Either one of these materials or a mixture thereof can be used in an amount of 0 to 30% by weight, preferably 5 to 15% by weight, of the total monomers.

The film-forming resin of the present invention may be produced by combining the above-mentioned monomers and copolymerizing them in the presence of a radical polymerization initiator by a known polymerization technique such as bulk polymerization, solution polymerization, suspension polymerization or emulsion polymerization. Among these methods, solution polymerization is advantageous in particular. In the solution polymerization, a water-miscible organic solvent or a water-mixture thereof is preferably employed. Either one of such an organic solvent or a mixture thereof may be used. Examples of the water-miscible organic solvent include aliphatic alcohols having 1 to 3 carbon atoms such as methanol, ethanol and propanol; ketones such as acetone and methyl ethyl ketone; and ethers such as tetrahydrofuran, glyme, diglyme and dioxane. In particular, methanol, ethanol, acetone and water-mixtures thereof are preferable.

Appropriate examples of the radical polymerization initiator to be used in the present invention include azo compounds such as 2,2'-azobisisobutylonitrile, 2,2'-azobis(2,4-dimethylvaleronitrile) (hereinafter referred to as "V-65"), 2,2'-azobis(4-methoxy-2,4- dimethylvaleronitrile), dimethyl-2,2'-azobisisobutylate, 2,2'-azobis(2-methylbutylonitrile) and 1,1'-azobis(1-cyclohexanecarbonitrile). Further, organic peroxides such as t-butyl peroctate, dicumyl peroxide, di-t-butyl peroxide and dibenzoyl peroxide may be used therefor. In this case, however, it is difficult to control the reaction conditions, since such a an organic peroxide might undergo a redox reaction with the tertiary amino group of the monomer (III). Therefore, the reaction should be conducted, for example, at a temperature lower than 40° C. Thus it is not preferable from an industrial viewpoint to use these organic peroxides as the radical polymerization initiator. The radical polymerization initiator may be preferably used in an amount of from 0.001 to 2.0% by mol, more preferably from 0.01 to 1.0% by mol, of the monomer mixture.

The polymerization may be conducted by feeding all of the monomer mixture and the radical polymerization initiator and then heating the reaction mixture. Alternately, each monomer and/or the radical polymerization initiator can be optionally added dropwise or by portionwise so as to carry out the polymerization.

The polymerization temperature may be appropriately determined depending on the employed radical polymerization initiator, monomers and solvent. Generally speaking, it may range from 30° to 100° C., preferably from 50° to 90° C. The copolymerization may be conducted under an inert gas atmosphere such as a nitrogen atmosphere, as commonly effected in the art. Details of the production of the copolymer of the present invention is further described, for example, in British Patent GB 1,407,659.

After the completion of the polymerization stage, the resulting copolymer may be isolated from the reaction mixture by a conventional method such as reprecipitation or solvent distillation. Further, the unreacted monomers can be removed from the obtained copolymer by a conventional method, for example, repeating reprecipitation, membrane-separation, chromatography or extraction. The weight-average molecular weight of the copolymer thus obtained, which is determined by gel filtration chromatography and expressed in terms of polystyrene, can be controlled within a range of from 1,000 to 1,000,000 by appropriately selecting the polymerization conditions. In order to achieve the object of the present invention, the copolymer product having a weight-average molecular weight of from 100,000 to 500,000, preferably from 20,000 to 200,000, is employed.

The tertiary amino group of the copolymer thus obtained may be neutralized with an inorganic or organic acid to make the copolymer soluble in water. In this case, it is preferable to neutralize 50% or more of the total tertiary amino groups. Examples of the inorganic acid include hydrochloric acid, sulfuric acid and phosphoric acid, and examples of the organic acid include acetic acid, glycolic acid, lactic acid, dimethylolpropionic acid, tartaric acid, citric acid, maleic acid and malic acid.

Examples of the hair dressing composition, which is one embodiment of the present invention include a hair spray, a set foam, a set lotion, a jell, a shampoo or a rinse, and it can be in the form of, for example, an aqueous solution, an aqueous alcoholic solution, an emulsion, a cream or a gel. These hair dressing compositions can be roughly classified into those containing a propellant such as hair spray or set form, and those free from any propellant such as set lotion, hair set jell, shampoo or rinse. The hair dressing composition of the present invention is preferably the former type, namely, containing a propellant.

A hair dressing composition containing a propellant may preferably contain 0.01 to 15% by weight, more preferably 2 to 6% by weight, of the film-forming resin of the present invention, 50 to 99.8% by weight of solvent(s) selected from among lower alcohols such as ethanol, polyols and water and 0.1 to 20% by weight of oil(s) selected from among hydrocarbons, ester oils, silicone and its derivatives and natural fats and oils. In addition, 0.5 to 3.0% by weight of texture improver(s) selected from among higher alcohols, myristic acid, octyldodecyl, glycerol, polyethylene glycol and polyoxyethylene hexadecyl ether and 0.1 to 3.0% by weight of film-forming aid(s) such as alkylene oxide-added alkyl ethers such as polyoxyethylene stearyl ether or cationic polymers such as cationic cellulose can be contained in the hair dressing composition of the present invention.

As the propellant, either pure LPG, Pure Freon gas, pure dimethyl ether (DME), a mixture of LPG and Freon and a mixture of DME and Freon gas can be employed. It is particularly preferable to use the film-forming resin of the present invention together with a propellant comprising 50 to 100% of LPG. The ratio of the stock solution to the propellant is within the range of from 5/95 to 70/30, preferably from 20/80 to 50/50.

When the hair dressing composition of the present invention is to be formulated into a gel, for example, a hair set jell, the hair dressing composition preferably comprises 0.5 to 10.0% by weight, more preferably 1.0 to 3.0% by weight, of the film-forming resin, 0.5 to 2.0% by weight of a thickener selected from among, for example, water-soluble polymers such as polyacrylate or hydroxyethylcellulose and a solvent comprising purified water optionally together with a lower alcohol.

In the case of a shampoo or a rinse, the film-forming resin of the present invention can be used in an amount of 0.1 to 5.0% by weight, preferably 0.5 to 2.0% by weight.

In addition, these hair dressing composition may further contain various additives conventionally employed in the art, for example, active ingredients such as preservatives, UV absorbers, metallic ion sequestering agents and anti-dandruff agents, colorants and perfumes, if required.

The film-forming resin of the present invention, which is highly compatible in LPG, is available in the replacement of Freon gas by LPG. Furthermore, it is highly soluble not only in hydrocarbon solvents such as LPG but also in other organic solvents such as aromatic ones, halogenated ones, ketones and esters, which makes it widely applicable. For example, the film-forming resin of the present invention is available as a surface treatment agent for natural or synthetic leather, rubber, plastics and glass to thereby impart an excellent texture, luster and gloss to these substrates. Further, it can impart, for example, a defogging and antistatic effect, when the composition is appropriately selected. It is also available in manicuring, since it shows a good adhesion to protein materials such as nail or skin. It is particularly noted that the film-forming resin of the present invention wherein the tertiary amino group is neutralized can be made water-soluble. Thus it can be readily removed by simply washing with water. Thus the film-forming resin of the present invention can be applied to various purposes by appropriately selecting the composition thereof.

The hair dressing composition of the present invention sustains an excellent setting effect and set-retention not only under common conditions but also under highly humid conditions. Further it can be readily washed away with a shampoo. Furthermore, it gives an excellent texture after spraying.

To further illustrate the present invention, and not by way of limitation, the following Synthetic Examples on the film-forming resin and Examples on the hair dressing composition will be given. Unless otherwise indicated, all parts, ratios and percents are by weight.

SYNTHETIC EXAMPLES 1 to 12

100 parts of ethanol was introduced into a four-neck flask provided with a reflux condenser, dropping funnels, a thermometer, a nitrogen inlet and a stirrer and heated therein to 60° C. Next, a monomer solution comprising 100 parts of a monomer mixture and 200 parts of ethanol optionally together with water and an initiator solution prepared by dissolving an initiator in 33 parts of ethanol were simultaneously added dropwise thereto within 1.5 hour under a nitrogen atmosphere. The resulting mixture was allowed to react under the temperature of 60° C. while stirring for additional 8 hours. After the polymerization, the product was purified by reprecipitating in water and dried under reduced pressure (20 mmHg) at 80° C. for 12 hours. The polymer thus obtained was in the form of a pale yellow solid. The weight-average molecular weight of the polymer of Synthetic Example 1 was 104,300 (in terms of GPC: polystyrene in a tetrahydrofuran solution). The weight-average molecular weights of the polymers of Synthetic Examples 2 to 12 ranged from 60,000 to 160,000. Table 1 shows the monomer composition of each polymer.

TABLE 1

| | Synthetic Example | | | | | | | | | | | |
| --- | --- | --- | --- | --- | --- | --- | --- | --- | --- | --- | --- | --- |
| | 1 (%) | 2 (%) | 3 (%) | 4 (%) | 5 (%) | 6 (%) | 7 (%) | 8 (%) | 9 (%) | 10 (%) | 11 (%) | 12 (%) |
| Monomer Composition*[1]) | | | | | | | | | | | | |
| Monomer (I) | | | | | | | | | | | | |
| N-t-Butylacrylamide | 55 | 65 | 55 | 55 | 50 | 50 | | | 70 | 45 | 55 | 60 |

TABLE 1-continued

| | Synthetic Example | | | | | | | | | | | |
|---|---|---|---|---|---|---|---|---|---|---|---|---|
| | 1 (%) | 2 (%) | 3 (%) | 4 (%) | 5 (%) | 6 (%) | 7 (%) | 8 (%) | 9 (%) | 10 (%) | 11 (%) | 12 (%) |
| (t-BuAAm) | | | | | | | | | | | | |
| N-t-Octylacrylamide | | | | | | | 40 | 50 | | | | |
| Monomer (II) | | | | | | | | | | | | |
| Ethyl acrylate (EA) | 25 | | 25 | 25 | 30 | 32 | | | 10 | 35 | 30 | 27 |
| Methyl methacrylate (MMA) | | 15 | | | | | | | | | | |
| n-Buthyl acrylate (n-BuA) | | | | | | | 30 | 20 | | | | |
| Monomer (III) | | | | | | | | | | | | |
| N,N-Dimethylaminoethyl acrylate (DMAEA) | 10 | 10 | | | 10 | 10 | 15 | | 10 | 10 | 10 | |
| N,N-Diethylaminoethyl methacrylate (DEAEMA) | | | 10 | | | | | 15 | | | | |
| N,N-Dimethylaminopropyl acrylamide (DMAPAAm) | | | | 10 | | | | | | | | 13 |
| Monomer (IV) | | | | | | | | | | | | |
| Methoxylpolyethylene glycol (PEG400)*3) methacrylate (PEGMA) | 10 | 10 | 10 | | | | 15 | | 10 | 10 | 5 | |
| Methoxylpolyethylene glycol (PEG1000)*4) acrylate | | | | 10 | | | | 15 | | | | |
| Methoxypolypropylene glycol (PPG600)*5) acrylate | | | | | 10 | | | | | | | |
| 2-Hydroxyethyl methacrylate (HEMA) | | | | | | 8 | | | | | | |
| **Initiator*2)** | | | | | | | | | | | | |
| 2,2-Azobis-(2,4-dimethyl-valeronitrile) (V-65) | 0.26 | 0.26 | 0.26 | 0.26 | 0.26 | | 0.26 | 0.26 | 0.26 | 0.26 | | |
| Azobisisobutylonitrile (AIBN) | | | | | | 0.26 | | | | | 0.5 | 0.5 |

Notes:
*1)expressed in % by weight per total weight of monomers.
*2)expressed in % by mol per total mol of monomers
*3)the abbreviation "(PEG 400)" as used herein means "a mean polymerization degree of polyethylene glycol of 40".
*4)the abbreviation "(PEG 1000)" as used herein means "a mean polymerization degree of polyethylene glycol of 100".
*5)the abbreviation "(PEG 600)" as used herein means "a mean polymerization degree of polypropylene glycol of 60).

EXAMPLE 1

1.5 parts of the copolymer obtained in Synthetic Example 1 was dissolved in 32.988 parts of absolute ethanol. 0.062 part of glycolic acid, 0.3 part of an oil (dimethyl polysiloxane) and 0.15 part of a perfume were added thereto. The obtained solution was introduced into an aerosol container and 56.55 parts of Freon gas and 8.45 parts of LPG were pressed therein so as to give an aerosol composition.

EXAMPLES 2 TO 10

The procedure of Example 1 was repeated with the use of the components specified in Table 2 to thereby give an aerosol composition.

TABLE 2

| | EXAMPLES | | | | | | | | | |
|---|---|---|---|---|---|---|---|---|---|---|
| | 1 (%) | 2 (%) | 3 (%) | 4 (%) | 5 (%) | 6 (%) | 7 (%) | 8 (%) | 9 (%) | 10 (%) |
| Copolymer | | | | | | | | | | |
| 1 | 1.5 | | | | | | | | | |
| 2 | | 1.5 | | | | | | | | |
| 3 | | | 1.5 | | | | | | | |
| 4 | | | | 1.5 | | | | | | |
| 5 | | | | | 1.5 | | | | | |
| 6 | | | | | | 1.5 | | | | |
| 7 | | | | | | | 1.5 | | | |
| 8 | | | | | | | | 1.5 | | |
| 9 | | | | | | | | | 1.5 | |
| 10 | | | | | | | | | | 1.5 |
| Neutrizing Agent | | | | | | | | | | |
| Lactic acid | | 0.092 | | | 0.074 | | | 0.074 | 0.074 | 0.074 |
| Glycolic acid | 0.062 | | | | | 0.062 | | | | |
| Dimethylol glycolic acid | | | 0.11 | 0.11 | | | 0.11 | | | |
| Dimethyl polysiloxane | 0.3 | 0.3 | 0.3 | 0.3 | 0.3 | 0.3 | 0.3 | 0.3 | 0.3 | 0.3 |
| Perfume | 0.15 | 0.15 | 0.15 | 0.15 | 0.15 | 0.15 | 0.15 | 0.15 | 0.15 | 0.15 |
| Absolute ethanol | 32.988 | 32.958 | 32.94 | 32.94 | 32.976 | 32.988 | 32.94 | 32.976 | 32.976 | 32.976 |
| Propellant | | | | | | | | | | |
| Freon 11 | | | | 28.275 | | | | | | |
| Freon 12 | 56.55 | | | 28.275 | | | | | | |
| LPG | 8.45 | 65.0 | 65.0 | 8.45 | 65.0 | 65.0 | 65.0 | 65.0 | 65.0 | |
| DME | | | | | | | | | | 65.0 |

TABLE 2-continued

| | EXAMPLES | | | | | | | | | |
|---|---|---|---|---|---|---|---|---|---|---|
| | 1 (%) | 2 (%) | 3 (%) | 4 (%) | 5 (%) | 6 (%) | 7 (%) | 8 (%) | 9 (%) | 10 (%) |
| Total | 100.0 | 100.0 | 100.0 | 100.0 | 100.0 | 100.0 | 100.0 | 100.0 | 100.0 | 100.0 |

Note: all values indicated in the above table are % by weight.

EXAMPLE 11

The following components were mixed to thereby give a hair set lotion:

| | (% by weight) |
|---|---|
| copolymer of Synthetic Example 1 | 2.0 |
| polyether-denatured silicone | 1.0 |
| lactic acid | 0.12 |
| ethanol | 86.38 |
| purified water | 10.0 |
| perfume | 0.5 |
| Total | 100.0. |

EXAMPLE 12

The following components were mixed to thereby give a hair shampoo:

| | (% by weight) |
|---|---|
| laurylpolyoxyethylene sulfate triethanolamine salt (40% aqueous solution) | 32.0 |
| lauroyldiethanolamide | 4.0 |
| polyethylene glycol | 1.0 |
| copolymer of Synthetic Example 2 | 1.0 |
| lactic acid | 0.11 |
| purified water | 61.39 |
| perfume | 0.5 |
| Total | 100.0. |

EXAMPLE 13

The following components were mixed to thereby give a hair set jell:

| | (% by weight) |
|---|---|
| copolymer of Synthetic Example 2 | 2.0 |
| lactic acid | 0.1 |
| purified water | 80.0 |
| Carbopol 940 | 0.5 |
| triethanolamine | 0.5 |
| ethanol | 16.7 |
| perfume | 0.2 |
| Total | 100.0. |

EXAMPLE 14

The following components were mixed to thereby give a hair set foam:

| Stock solution: | (% by weight) |
|---|---|
| copolymer of Synthetic Example 1 | 3.0 |
| polyoxyethylene hexadecyl ether | 0.5 |
| polyether-denatured silicone | 1.5 |
| ethanol | 10.0 |
| purified water | 84.65 |
| perfume | 0.2 |
| lactic acid | 0.15 |

| Stock solution: | (% by weight) |
|---|---|
| Total | 100.0 |

Propellant: LPG 100%
Stock solution/Propellant = 90/10.

EXAMPLE 15

The following components were mixed to thereby give a hair rinse:

| | (% by weight) |
|---|---|
| copolymer of Synthetic Example 1 | 1.0 |
| glycolic acid | 0.04 |
| stearyltrimethylammonium chloride | 2.0 |
| cetyl alcohol | 2.0 |
| purified water | 94.76 |
| perfume | 0.2 |
| Total | 100.0. |

EXAMPLE 16

The products of Examples 1, 2 and 3 and a marketed hair spray A (wherein a mixture of polyvinyl pyrrolidone(PVP) and vinyl acetate (VAc) (6/4) was used as a film-forming resin), and film-forming resins contained therein were evaluated in the following manner.

(1) Set-retention

A hair bundle (length: 18 cm, weight: 1.5 g) was moisten with water, wound around a rod (diameter: 2 cm) and allowed to dry. After drying, the hair thus curled was removed from the rod and an aerosol composition was sprayed thereon at a distance of 15 cm. After drying, the hair was hung in a thermo-hydrostat (20° C., 98% RH) for 30 minutes. Then the elongation of the curl was observed and thus the curl-retention ratio was evaluated. This curl-retention ratio was affected by the set-retention. FIG. 1 shows the results.

(2) Compatibility of film-forming resin with propellant

The film-forming resins obtained in Synthetic Examples 1, 2 and 3 were subjected a neutralization by adding each resins into ethanol solution dissolving a neutralizing agent (glycolic acid) to obtain resin solutions in intended concentration.

The resulting neutralized products of resins of Synthetic Examples 1, 2 and 3, and a mixture of PVP and VAc (6/4) were formulated into 20% solutions in ethanol. Each solution thus obtained was introduced into a transparent glass bottle. Then a propellant (LPG) was pressed therein and the compatibility of the film-forming resin with the propellant was evaluated based on the amount of the LPG when a precipitate was observed.

Table 3 shows the results.

TABLE 3

| | Synthetic Example | Marketed Product |
|---|---|---|

TABLE 3-continued

|  | 1 | 2 | 3 | A |
|---|---|---|---|---|
| Compatibility | o | o | o | x |

Criteria:
o: Good (200% by weight or more based on the ethanol solution).
Δ: Moderate (100 to 200% by weight based thereon).
x: Poor (less than 200% by weight based thereon).

(3) Evaluation of texture

The hair spray of Example 1 and the marketed one A were sprayed onto a model wig and the textures were evaluated.

Table 4 shows the results.

TABLE 4

|  | Example 1 | Marketed Product 1 |
|---|---|---|
| General evaluation | A | D |
| Smoothness | B | C |
| Coarseness | B | D |
| Setting | B | D |
| Set-retention under humid condition | A | E |
| Easiness in washing away | B | C |

Criteria:
A: Very good.
B: Good.
C: Moderate.
D: Somewhat poor.
E: Poor.

What is claimed is:

1. A film-forming resin which is a copolymer consisting essentially of the following monomers (a) to (d):

(a) 30 to 80% by weight of a (meth)acrylamide monomer represented by the following formula (I):

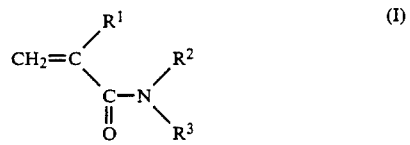

wherein $R^1$ represents a hydrogen atom or a methyl group; and
    $R^2$ and $R^3$ may be either the same or different from each other and each represents a hydrogen atom or an alkyl group having 4 to 12 carbon atoms, or $R^2$ and $R^3$ form a ring together with the adjacent nitrogen atom;

(b) 5 to 45% by weight of a (meth)acrylate monomer represented by the following formula (II):

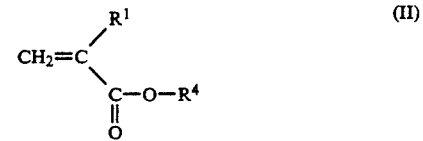

wherein $R^1$ is as defined above; and $R^4$ represents an alkyl group having 1 to 4 carbon atoms;

(c) 2 to 30% by weight of a (meth)acrylate monomer and/or a (meth)acrylamide monomer having a tertiary amino group represented by the following formula (III):

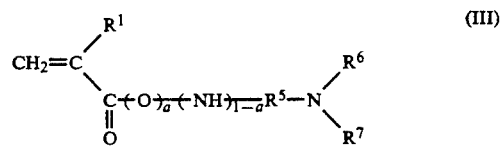

wherein $R^1$ is as defined above; $R^5$ represents an alkylene group having 2 or 3 carbon atoms;
    $R^6$ and $R^7$ may be either the same or different from each other and each represents a methyl or an ethyl group; and
    a is an integer of 0 or 1;
    and (d) 0 to 30% by weight of a (meth)acrylate monomer represented by the following formula (IV):

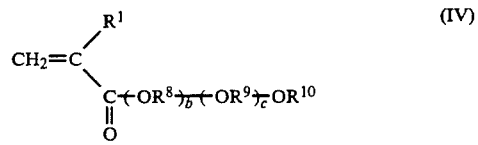

wherein $R^1$ is as defined above;
    $R^8$ and $R^9$ are different from each other and each represents an alkylene group having 2 to 4 carbon atoms;
    $R^{10}$ represents a hydrogen atom or a methyl group; and
    b and c are each an integer of 0 to 50, provided that b and c are not 0 at the same time.

2. The film-forming resin as claimed in claim 1, wherein at least 50% of the tertiary amino groups of said copolymer are neutralized with an inorganic or organic acid.

3. A hair dressing composition containing a film-forming resin as claimed in claim 1.

4. A hair dressing composition containing a film-forming resin as claimed in claim 2.

5. The film-forming resin as claimed in claim 1, which has (d) 5 to 15% by weight of a (meth)acrylate monomer represented by the formula (IV).

* * * * *